United States Patent
Schäfer et al.

(10) Patent No.: US 10,213,706 B2
(45) Date of Patent: Feb. 26, 2019

(54) PROCESS AND APPARATUS FOR PURIFICATION OF ACRYLIC ACID

(71) Applicant: Sulzer Chemtech AG, Winterthur (CH)

(72) Inventors: Matthias Schäfer, Kreuzlingen (CH); Andrzej Kuszlik, Buchs (CH); Florian Lippuner, Gams (CH); Herbert Engstler, Frastanz (AT)

(73) Assignee: Sulzer Chemtech AG, Winterthur (CH)

( * ) Notice: Subject to any disclaimer, the term of this patent is extended or adjusted under 35 U.S.C. 154(b) by 0 days.

(21) Appl. No.: 15/520,038

(22) PCT Filed: Jul. 30, 2015

(86) PCT No.: PCT/EP2015/067495
§ 371 (c)(1),
(2) Date: Apr. 18, 2017

(87) PCT Pub. No.: WO2016/062422
PCT Pub. Date: Apr. 28, 2016

(65) Prior Publication Data
US 2017/0326471 A1    Nov. 16, 2017

(30) Foreign Application Priority Data
Oct. 24, 2014   (EP) .................................... 14190231

(51) Int. Cl.
*B01D 11/00*     (2006.01)
*B01D 21/00*     (2006.01)
(Continued)

(52) U.S. Cl.
CPC ............ *B01D 9/0059* (2013.01); *C07C 51/43* (2013.01); *C07C 57/04* (2013.01)

(58) Field of Classification Search
CPC .... C08F 2500/20; C08F 210/06; C30B 29/58; C07C 51/43; C07C 51/44
(Continued)

(56) References Cited

U.S. PATENT DOCUMENTS 5,498,749 A * 3/1996 Heise .................... C07C 67/03
560/78
5,504,247 A   4/1996 Saxer et al.
(Continued)

FOREIGN PATENT DOCUMENTS

CN         1121373 C    12/1997
CN         1265640 A     9/2000
(Continued)

*Primary Examiner* — Monzer R Chorbaji
(74) *Attorney, Agent, or Firm* — Larson & Anderson, LLC

(57) ABSTRACT

A process and an apparatus for the purification of a crude acrylic acid composition containing maleic anhydride as an impurity comprising the following steps: (a) carrying out at least one dynamic melt crystallization stage (14, 14a, 14b, 14c, 14d) with the crude acrylic acid composition to prepare a first purified acrylic acid composition and a first residue containing at least 3.5% by weight maleic anhydride, (b) adding a solvent (26) which is capable of dissolving maleic anhydride to the first residue in an amount that the weight ratio of the solvent to the maleic anhydride is 0.3 or more to prepare a ratio-adjusted residue and (c) carrying out at least one further dynamic melt crystallization stage and/or at least one static melt crystallization stage (18, 18a, 18b) with the ratio-adjusted residue to prepare a second purified acrylic acid composition and a second residue.

15 Claims, 1 Drawing Sheet

Figure 1:
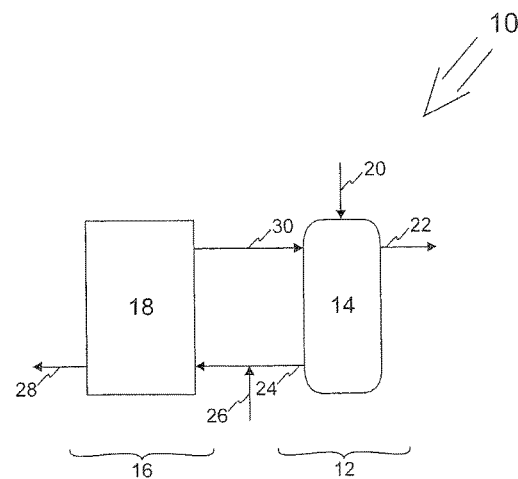

(51) Int. Cl.
*C07C 51/43* (2006.01)
*B01D 9/00* (2006.01)
*C07C 57/04* (2006.01)

(58) Field of Classification Search
USPC ........... 422/256, 260; 210/634, 774, 702; 560/78; 554/211; 260/486, 600
See application file for complete search history.

(56) References Cited

U.S. PATENT DOCUMENTS

| | | |
|---|---|---|
| 5,831,124 A | 11/1998 | Machhammer et al. |
| 6,063,959 A | 5/2000 | Lehnert et al. |
| 6,380,427 B1 | 4/2002 | Miyazaki et al. |
| 6,448,439 B1 | 9/2002 | Eck et al. |
| 6,541,665 B1 | 4/2003 | Bastiaensen et al. |
| 6,596,901 B1 | 7/2003 | Eck et al. |
| 6,664,419 B1 | 12/2003 | Bub |
| 6,700,016 B1 | 3/2004 | Eck et al. |
| 6,852,881 B2 | 2/2005 | De Decker et al. |
| 7,112,695 B2 | 9/2006 | Eck et al. |
| 7,196,215 B2 | 3/2007 | Lin et al. |
| 7,307,132 B2 | 12/2007 | Nestler et al. |
| 7,307,189 B2 | 12/2007 | Eck et al. |
| 7,381,839 B2 | 6/2008 | Ueno et al. |
| 7,557,245 B2 | 7/2009 | Nordhoff et al. |
| 7,557,246 B2 | 7/2009 | Nordhoff et al. |
| 7,803,969 B2 | 9/2010 | Nordhoff et al. |
| 8,198,481 B2 | 6/2012 | Kuppinger et al. |
| 8,231,792 B2 | 7/2012 | Fiene et al. |
| 8,637,701 B2 | 1/2014 | Kitaura |
| 8,680,330 B2 | 3/2014 | Sakamoto et al. |
| 8,680,331 B2 | 3/2014 | Sakamoto et al. |
| 8,859,809 B2 | 10/2014 | Sakamoto et al. |
| 2008/0183014 A1* | 7/2008 | Diefenbacher ......... C07C 51/44 562/600 |
| 2009/0076303 A1 | 3/2009 | Han et al. |
| 2013/0178652 A1 | 7/2013 | Fruchey et al. |
| 2013/0274520 A1 | 10/2013 | Godlewski et al. |
| 2014/0180234 A1 | 6/2014 | Bub et al. |

FOREIGN PATENT DOCUMENTS

| | | | |
|---|---|---|---|
| CN | 102428065 A | 4/2012 | |
| CN | 102471213 A | 5/2012 | |
| EP | 0 616 998 B1 | 9/1994 | |
| EP | 1 150 759 B1 | 11/2001 | |
| EP | 1 286 943 B1 | 3/2003 | |
| EP | 1 795 521 A1 | 6/2007 | |
| EP | 2 450 339 A1 | 5/2012 | |
| EP | 2 450 341 A1 | 5/2012 | |
| WO | 02/098836 A1 | 12/2002 | |
| WO | WO-02098836 A1 * | 12/2002 | ............ C07C 51/43 |
| WO | WO2002098836 * | 12/2002 | |
| WO | 03/095510 A1 | 11/2003 | |
| WO | 2006/092405 A1 | 9/2006 | |

* cited by examiner

PROCESS AND APPARATUS FOR PURIFICATION OF ACRYLIC ACID

The present invention relates to a process and an apparatus for the purification of acrylic acid.

Acrylic acid is an important starting material for the preparation of polymers in the plastics industry. Not only acrylic acid as such, but also the esters and the salts of acrylic acid are important monomers for the preparation of polymers having a wide range of application. For example, acrylic acid as well as the esters and salts derived therefrom are used for the preparation of adhesives, superabsorbent polymers, binders, textile fibers, surface coatings, foams and composite materials.

At present, acrylic acid is commonly produced by catalytic oxidation of propylene in the gas phase using an oxygen-containing gas. This oxidation can be performed as a two-step process, wherein in a first step propylene is reacted with air as the oxygen-containing gas in the presence of e.g. a bismuth molybdenum oxide catalyst at a temperature of about 300° C. to give acrolein, which is subsequently converted in a second step to acrylic acid by a second oxidation using air and e.g. a molybdenum vanadium oxide catalyst at a temperature of about 250° C. to about 300° C. The obtained acrylic acid, which is present in a gaseous mixture in admixture with the reactants, is then usually extracted from the gas phase by absorption making use of a solvent, such as water or a high-boiling ester. Afterwards, the solvent of the absorption step can be separated by distillation, whereby a crude acrylic acid composition is formed.

Although the purity of such a crude acrylic acid can be as high as 99%, the crude acrylic acid still contains after the distillation step impurities, such as, for example, acetic acid, propionic acid, maleic acid, maleic anhydride, acrolein, furfural, benzaldehyde, phenothiazine and protoanemonin. However, such impurities are in particular disadvantageous, because these impurities at least partially inhibit the polymerization of the acrylic acid, so that the amount of residual monomers in the resulting acrylic acid polymer increases. This is in particular undesirable, when the acrylic acid is used for the production of superabsorbent polymers, which are, for example, used in sanitary articles. In addition, the absorption properties of the acrylic acid polymer are deteriorated in the case that the acrylic acid used for the polymerization contains impurities.

Therefore, a further purification of the crude acrylic acid is in general required. Both, distillation and melt crystallization are suitable methods therefor. However, if melt crystallization is used for the further purification of a crude acrylic acid composition, at least a part of the impurities may precipitate during the crystallization process due to their low solubility in acryl acid. Such a precipitation occurs in particular, when maleic anhydride is present in the crude acrylic acid composition as impurity. In this case, the precipitate of maleic anhydride accumulates in the crystallization equipment, which is also due to the higher melting point of maleic anhydride, which is 53° C., compared to that of acrylic acid, which is 14° C. In addition, the precipitate of maleic anhydride can block the conduits and the valves of the crystallization equipment. Consequently, a discharge of the precipitate of maleic anhydride from the crystallization equipment is required in order to restore the capacity of the crystallizer and the function of the conduits and valves, which is, however, time consuming as well as expensive and leads to a temporary downtime of the equipment. The aforementioned problems due to the precipitation of maleic anhydride are in particular challenging when the concentration of maleic anhydride in the composition is during the crystallization 3.5% by weight or more.

One option for the removal of the precipitate of maleic anhydride from the crystallization equipment is to shut down the crystallization plant and to flush it with a suitable solvent in order to dissolve the maleic anhydride and to discharge it from the equipment. However, since the production of purified acrylic acid has to be interrupted and the shut-down and the start-up of the crystallization plant require considerable technical effort and time, such a shut-down for removing precipitated maleic anhydride is disadvantageous in particular from an economical point of view.

On the other hand, it has been also proposed to keep the impurities during the crystallization process in solution, in order to avoid a precipitation of the impurities during the crystallization. For example, EP 1 150 759 B1 discloses a method, in which a solvent, such as water, is added to the crude acrylic acid composition before the crystallization in an amount, which is sufficient to prevent a precipitation of maleic anhydride in the crude acrylic acid composition and thus to keep these compounds in solution. However, since the solvent is added to the crude acrylic acid before the crystallization and therefore to the whole feed, a considerably high amount of the solvent is required in order to keep the maleic anhydride in solution as well as during the whole crystallization process. This is especially disadvantageous as the water hinders the crystal growth of acrylic acid, thereby leading to smaller crystals with a higher surface area. The high surface area is disadvantageous for the purification of the acrylic acid as the amount of impurities attached to the surface will increase, too. As a further disadvantage, also the amount of energy, which has to be transferred from the and to the composition during the heating and cooling cycles of the crystallization process, is high, because the amount of the acrylic acid composition is increased as a consequence of the addition of the high amounts of solvent. Consequently, the heating and cooling cycles consume a considerable amount of energy in this process.

Apparatuses having two crystallization vessels and agitation devices such as impellers and thus suitable for evaporative crystallization processes are known, for example from WO 02/098836 A1, which discloses an evaporative crystallization process for the production of purified TPA beginning with the oxidation of p-xylene. The crystallization vessels of WO '836 feature a second outlet for removal of solvent as a vapor from the crystallizer, which is subsequently condensed and returned to the crystallization zone (solvent recirculation loop). Such apparatuses may be suitable for the evaporative crystallization (precipitation) out of dilute solutions, such as those containing 10-35% by weight dissolved TPA. However such apparatuses are unsuitable for the further purification of a solvent-free substance, such as a crude acrylic acid, which may have a purity as high as 99% by weight.

Taking all this into account, the object underlying the present invention is to provide a process for the purification of a crude acrylic acid composition comprising maleic anhydride as an impurity, which overcomes the aforementioned problems, i.e. to provide a process for the purification of a crude acrylic acid composition comprising maleic anhydride as an impurity, which needs considerably less solvent and requires significantly less energy and which can be performed in a plant with less complex crystallization equipment and comparably low investment costs than the processes known in the prior art.

In accordance with the present invention, a "source of a crude acrylic acid composition" may be, for example, a chemical plant for the catalytic oxidation of propylene in the gas phase using an oxygen-containing gas, preferably in a two-step process. In another embodiment, a source may be a chemical plant in which a renewable starting material, such as from hydroxypropionic acid, a hydroxypropionic acid derivative or glycerol is prepared by means of fermentation, followed by dehydration in the presence of a catalyst and subsequent water removal, e.g., by means of azeotropic distillation.

In accordance with the present invention, the term "crystallization stage" in reference to a purification process refers to one purification cycle of crystallizing and subsequent melting. In some processes such as falling film or static melt crystallizations, the "crystallization stage" may optionally comprise an intermediate sweating operation to remove adhered impurities from the crystals. One skilled in the art will understand that two or more crystallization stages can be carried out in one or more crystallizers, for example, in a batch process. Alternatively, each crystallization stage may be carried out in a separate crystallizer, e.g. in a continuous purification process.

In accordance with the present invention, the term "melt crystallization section" in reference to an apparatus for a purification process refers to one or more crystallizers of the same type (e.g. falling film, static melt, or suspension).

In accordance with the present invention this object is satisfied by providing a process for the purification of a crude acrylic acid composition containing maleic anhydride as an impurity, wherein the process comprises the following steps:
  (a) carrying out at least one dynamic melt crystallization stage (14, 14a, 14b, 14c, 14d) with the crude acrylic acid composition to prepare a first purified acrylic acid composition and a first residue preferably containing at least 3.5% by weight maleic anhydride,
  (b) adding a solvent (26) which is capable of dissolving maleic anhydride to the first residue in an amount that the weight ratio of the solvent to the maleic anhydride is 0.3 or more to prepare a ratio-adjusted residue and
  (c) carrying out at least one further dynamic melt crystallization stage and/or at least one static melt crystallization stage (18, 18a, 18b) with the ratio-adjusted residue to prepare a second purified acrylic acid composition and a second residue.

This solution is based on the finding that by adding a solvent which is capable of dissolving maleic anhydride to the first residue obtained after the dynamic melt crystallization of step (a), wherein the first residue contains at least 3.5% by weight maleic anhydride, and that by adjusting the ratio of the weight of the solvent to the weight of the maleic anhydride in the first residue to 0.3 or more in step (b), the maleic anhydride is completely and reliably kept in solution, so that the so obtained ratio-adjusted residue can be used in a further crystallization stage without danger of a precipitation of maleic anhydride in the crystallization equipment. However, if the concentration of maleic anhydride in the first residue obtained in step (a) is less than 3.5% by weight, the degree of precipitation during the next crystallization stage performed in step (b) is comparably small and thus for the most applications acceptable.

In addition, the inventors have surprisingly found that the required amount of the solvent, which is needed to be added in step (b) to the first residue preferably containing at least 3.5% by weight maleic anhydride obtained after the dynamic melt crystallization of step (a) in order to keep the maleic anhydride in solution, is significantly less than in the case described in the prior art, in which the solvent is added to the feed crude acrylic acid composition before it is subjected to the melt crystallization process. Because the solvent is added in accordance with the present invention to the first residue and not to the feed crude acrylic acid composition, a hindrance of the crystal growth of acrylic acid due to the addition of water leading disadvantageously to smaller crystals with a higher surface area during the dynamic melt crystallization of step (a) is avoided. As set out above, such a high surface area is disadvantageous for the purification of the acrylic acid as the amount of impurities attached to the surface will increase, too. Moreover, because the solvent is added in accordance with the present invention to the first residue and not to the feed crude acrylic acid composition, the energy which has to be used for the heating and cooling cycles of the at least one dynamic melt crystallization stage (a) is considerable lower than in the case that the solvent is added already to the feed crude acrylic acid composition, because the volume of composition is due to the absence of solvent much lower than in the respective prior art methods, in which the solvent is added to the feed. Because the total amount of the solvent added to the first residue is lower than in the prior art processes, also the energy which has to be used for the heating and cooling cycles of at least one further melt crystallization stage (b) is lower than in the case that the solvent is added already to the feed crude acrylic acid composition. On account of all this, the energy balance of the process in accordance with the present invention is significantly better than in the aforementioned methods known in the prior art.

In advantage to prior art methods, in which precipitation of the maleic anhydride occurs during the crystallization, the plant for performing the method in accordance with the present invention does not need any means for separating precipitated maleic anhydride from the composition, so that a considerable less complex and less expensive crystallization plant can be used.

All in all, the process in accordance with the present invention allows an efficient preparation of a purified acrylic acid with low operation costs and with low investment costs.

In accordance with the present invention, the term "purified acrylic acid composition" refers to a composition which is obtained during a crystallization stage from a crude acrylic acid composition and which is enriched in acrylic acid compared to the crude acrylic acid composition before it has been subjected to said crystallization stage. Moreover, the term "residue" refers to a composition obtained during a crystallization stage from a crude acrylic acid composition and which is depleted in acrylic acid as compared to the acrylic acid composition before being subjected to the crystallization stage.

The content of a component, such as, for example, the content of maleic anhydride in the first residue, is preferably measured in accordance with the present invention by high-performance liquid-chromatography (HPLC). Thus, the weight ratio of the solvent to the maleic anhydride in the first residue is calculated from the respective contents measured by HPLC.

The dynamic melt crystallization stage, which is performed in step (a) of the melt crystallization, is not particularly limited and thus any dynamic melt crystallization known to a person skilled in the art may be employed therefor. In principle, dynamic melt crystallization is any melt crystallization process, which is carried out with forced movement of the liquid phase. Particular suitable dynamic melt crystallization methods in accordance with the present invention are, for example, falling film crystallization, crystallization in a fully flowed-through tube and suspension crystallization. However, the use of falling film crystallization for the dynamic melt crystallization stage of step (a) is preferred. Falling film crystallization is advantageously faster than static crystallization and therefore falling film crystallization leads to a high capacity and is characterized by an easy operation since there is no crystal slurry handling and no filtration, by a high reliability and by low operation costs. One skilled in the art will understand that crystallization vessels equipped with impellers, as in WO '836 A1, are unsuitable for suspension crystallization of melts such as in the present invention because of the high amount of solids/crystals. Such suspension crystallization of melts having high solids instead commonly makes use of scrapers to scrape formed crystals off of a cooled wall. One skilled in the art will also understand that falling film and static melt crystallizers have no moving parts and thus lack impellers. Impellers would actually be unsuitable for such apparatuses as the impeller would potentially destroy the crystal layers or become encrusted by a crystal layer itself due to crystal agglomeration.

The number of melt crystallization stages performed in step (a) of the melt crystallization process is not particularly limited, provided that at least one dynamic melt crystallization stage is conducted. Preferably, in step (a) two to four dynamic melt crystallization stages are conducted, wherein it is particularly preferred that all dynamic melt crystallization stages are falling film crystallization steps. This allows maintaining an advantageous balance between a reasonable number of the melt crystallization stages, a high purity of the acrylic acid, reasonable space requirements for the equipment for carrying out the melt crystallization process, low energy consumption and a high capacity. More specifically, by this combination of melt crystallization stages a content of acrylic acid of at least 99% by weight, preferably of at least 99.5% by weight, more preferably of at least 99.8% by weight and most preferably of at least 99.9% by weight, in each case based on 100% by weight of a purified acrylic acid composition drawn off from the melt crystallization process, can be obtained.

The term "first purified acrylic acid composition" is used in accordance with the present invention independently from the number of melt crystallization stages performed in step (a) and in general denotes a purified acrylic acid composition, which is obtained after the last crystallization stage performed in step (a). Likewise, the term "first residue" denotes in accordance with the present invention the residue, which is obtained after the last crystallization stage performed in step (a), before it is admixed with the solvent in step (b).

As set out above, maleic anhydride included in the composition precipitates during the crystallization, wherein particular problems arise, when the concentration of maleic anhydride in the composition during the crystallization is 3.5% by weight or more. Consequently, the method in accordance with the present invention is in particular suitable, when the concentration of the maleic anhydride in the first residue prepared in step (a) is at least 3.5% by weight, preferably at least 4% by weight, more preferably at least 8% by weight, even more preferably at least 12% by weight and most preferably at least 16% by weight based on 100% by weight of the first residue, which is formed in step (a).

The method in accordance with the present invention is particularly suitable for the purification of a crude acrylic acid composition, which contains as impurities—apart from maleic anhydride—at least one compound selected from the group consisting of acetic acid, propionic acid, maleic acid, acrolein, furfural, benzaldehyde, phenothiazine, protoanemonine and any combinations thereof.

In accordance with the present invention the solvent is added to the first residue in step (b) of the melt crystallization process in such an amount that the weight ratio of the solvent to the maleic anhydride, i.e. the ratio of the weight of the solvent to the weight of the maleic anhydride, is 0.3 or more. Preferably, the weight ratio of the solvent to the maleic anhydride in step (b) is adjusted to at least 0.5, more preferably to at least 0.8 and most preferably to about 1.0. Moreover, it is preferred that the weight ratio of the solvent to the maleic anhydride in step (b) is adjusted to at most 2, more preferably to at most 1.5 and most preferably to at most 1.2. Consequently, it is preferred that the weight ratio of the solvent to the maleic anhydride in step (b) is adjusted to 0.3 to 2.0, more preferably to 0.5 to 1.5, even more preferably to 0.8 to 1.2 and most preferably to about 1.0. By setting one of the aforementioned upper limits for the weight ratio of the solvent to the maleic anhydride the amount of the solvent which is used in the melt crystallization process is minimized. This is an advantage from both an economic and ecological point of view, since the expenses for the solvent and the amount of waste are kept low. In addition, by minimizing the amount of the solvent, the amount of energy which has to be transferred to and from the ratio-adjusted residue during the process is minimized, so that energy required for the heating and cooling cycle of the additional crystallization can be saved. In addition, because the solvent is added in accordance with the present invention to the first residue and not to the feed crude acrylic acid composition a hindrance of the crystal growth of acrylic acid due to the addition of water leading disadvantageously to smaller crystals with a higher surface area during the dynamic melt crystallization of step (a) is avoided. As set out above, such a high surface area is disadvantageous for the purification of the acrylic acid as the amount of impurities attached to the surface will increase, too.

In accordance with a preferred embodiment of the present invention and in particular in the case when the weight ratio of the solvent to the maleic anhydride in step (b) is adjusted to about 1.0, the ratio-adjusted residue obtained in step (b) comprises from 4 to 16% by weight of maleic anhydride, from 4 to 16% by weight of the solvent, the balance to 100% by weight being acrylic acid and further impurities, preferably from 5 to 12% by weight of maleic anhydride, from 5 to 12% by weight of the solvent, the balance to 100% by weight being acrylic acid and further impurities, and more preferably from 8 to 10% by weight of maleic anhydride, from 8 to 10% by weight of the solvent, the balance to 100% by weight being acrylic acid and further impurities, in each case based on 100% by weight of the ratio-adjusted residue. Also in this embodiment, the further impurities may comprise at least one compound selected from the group consisting of acetic acid, maleic acid, acrolein, propionic acid, furfural, benzaldehyde, phenothiazine, protoanemonin and any combinations thereof.

In principle, the chemical nature of the solvent which is added in step (b) to the first residue to prepare the ratio-adjusted residue is not particularly limited as long as maleic anhydride is soluble in the solvent. Thus, any solvent or any solvent mixture which is capable of dissolving maleic anhydride can be used as the solvent in accordance with the present invention. Furthermore, the solvent should not react and/or interfere with the acrylic acid or the other impurities. Particular suitable solvents are aqueous solvents, such as water or a mixture of water with at least one compound selected from the group consisting of acetic acid, propionic acid, maleic acid, acrolein, furfural, benzaldehyde, phenothiazine, protoanemonine and arbitrary mixtures of two or more of the aforementioned compounds. However, from the viewpoint of its easy availability and non-toxicity water is preferably used as the solvent in all embodiments of the melt crystallization process. This is also due to the fact that maleic anhydride is at least partially hydrolyzed by water to maleic acid in the presence of water. Because the solubility of maleic acid in water is comparably high, the amount of water which is required in order to prevent the maleic anhydride from precipitating can be minimized.

In accordance with the present invention, the melt crystallization process further comprises a step (c) in which at least one further dynamic melt crystallization and/or at least one static melt crystallization is carried out with the ratio-adjusted residue to prepare a second purified acrylic acid composition and a second residue, in order to increase the yield of purified acrylic acid, according to a further preferred embodiment. If in step (c) a dynamic melt crystallization stage is used, this is preferably performed as falling film crystallization, as crystallization in a fully flowed-through tube or as suspension crystallization, wherein falling film crystallization is particularly preferred.

Alternatively and in fact preferably, one or more static melt crystallization stages are conducted in step (c). In contrast to dynamic crystallization, static crystallization is suitable for crystallizing highly viscous liquids, such as those resulting from the dynamic melt crystallization performed in step (a). Moreover, static crystallization has the advantage of high flexibility, of wide operating range, of easy operation since there is no crystal slurry handling and no filtration, of high reliability and of low operation costs due to the lack of moving parts.

Also, the number of melt crystallization stages performed in step (c) of the melt crystallization process is not particularly limited, provided that at least one dynamic melt crystallization stage or at least one static melt crystallization stage is conducted. Preferably, one to three crystallization stages are performed in step (c). This allows maintaining an advantageous balance between a reasonable number of the melt crystallization stages, a high purity of the acrylic acid, reasonable space requirements for the equipment for carrying out the melt crystallization process and low energy consumption. More specifically, by this combination of melt crystallization stages a content of acrylic acid of at least 99% by weight, preferably of at least 99.5% by weight, more preferably of at least 99.8% by weight and most preferably of at least 99.9% by weight, in each case based on 100% by weight of a first purified acrylic acid composition drawn off from the melt crystallization process, can be obtained. Moreover, as set out above it is particularly preferred that all melt crystallization stages of step (c) are carried out as static melt crystallization stages.

The term "second purified acrylic acid composition" is used independently from the number of melt crystallization stages performed in step (c) and denotes in accordance with the present invention a purified acrylic acid composition which is obtained in the last crystallization stage of step (c). Likewise, the term "second residue" denotes in accordance with the present invention a composition which is obtained in the last crystallization stage of step (c) and which is depleted in acrylic acid as compared to the acrylic acid composition before being subjected to the crystallization stage.

In order to achieve a particular high yield of purified acrylic acid and to benefit from the saving of energy to a very high extent, according to a particularly preferred embodiment of the present invention the melt crystallization process comprises the steps of:

(a) carrying out two to four dynamic melt crystallization stages with the crude acrylic acid composition to prepare a first purified acrylic acid composition and a first residue preferably containing at least 3.5% by weight maleic anhydride based on 100% by weight of the first residue, (b) adding water to the first residue in order to adjust the weight ratio of the solvent to the maleic anhydride to 0.3 or more to prepare a ratio-adjusted residue and (c) carrying out one to three static melt crystallization stages with the ratio-adjusted residue to prepare a second purified acrylic acid composition and a second residue.

In a further development of the present invention, the second purified acrylic acid composition obtained in the melt crystallization of the step (c), is at least partially recycled to the dynamic melt crystallization of step (a). This step increases the yield obtained with the method.

In order to minimize technical complexity, investment costs and the space required for the melt crystallization equipment, in accordance with an alternative embodiment of the melt crystallization process only one dynamic melt crystallization stage is used in step (a) to prepare the first purified acrylic acid composition and the first residue and only one static melt crystallization stage is carried out in step (c) with the ratio-adjusted residue. Although the number of crystallization stages is decreased, the method still results in a satisfactory purity of the purified acrylic acid. Also in this embodiment the dynamic melt crystallization stage of step (a) is preferably carried out using falling film crystallization.

In general, the present invention is not particularly limited concerning the method, with which the crude acrylic acid composition is produced. Therefore, a crude acrylic acid composition obtained by any method known to a person skilled in the art may be purified with the process in accordance with the present invention.

For example, the crude acrylic acid composition can be prepared by distillation of an acrylic acid containing mixture which is obtained by absorption of acrylic acid from a gas phase using an absorbent. The absorbent can be any absorbent that is suitable for the absorption of acrylic acid from a gas phase and is preferably the same solvent as added in step (b) of the melt crystallization process. During the distillation of this preparation process the crude acrylic acid composition is usually obtained as the bottom product of the distillation. An exemplary method for the preparation of acrylic acid in the gas phase, from which it is absorbed by using the absorbent, is the catalytic oxidation of propylene with oxygen, which may be provided using air. Acrylic acid produced from propylene may comprise significant amounts of ketones having double bonds, in particular protoanemonine. This compound can, on contact with skin, cause signs of poisoning. Therefore, an alternative process to obtain acrylic acid having a particularly low content in protoanemonine has been described in US 2014/0180234 A1. Here, the crude acrylic acid composition can be prepared from a renewable starting material, such as from hydroxypropionic acid, a hydroxypropionic acid derivative or glycerol by means of fermentation, followed by dehydration in the presence of a catalyst and subsequent water removal, e.g., by means of azeotropic distillation. The impurities included in the crude acrylic acid composition obtained in this way are mainly benzaldehyde, acetaldehyde, maleic acid or maleic anhydride, acetic acid, lactic acid and propanoic acid, such as described e.g. in US 2013/0274520 A1 and US 2014/0180234 A1.

As the inventors have found that it is sufficient to add the solvent to the first residue during step (b) in order to prevent the maleic anhydride from precipitating, preferably no additional solvent is added to the crude acrylic acid composition before it is subjected to step (a).

Since the addition of the solvent in step (b) and the adjustment of the weight ratio of the solvent to the maleic anhydride to 0.3 or more in step (b) assures reliably that the maleic anhydride is kept in solution and does not precipitate, preferably in steps (a) to (c) no separation of a precipitated maleic anhydride by a separation means, such as a filter, from the crude acrylic acid composition or from the first residue nor any cleaning and/or shut-down of the plant is conducted.

Furthermore, the present invention is related to an apparatus for the purification of a crude acrylic acid composition containing maleic anhydride as an impurity using a melt crystallization process, preferably a melt crystallization process of any one of the preceding claims, wherein the apparatus comprises:
  a first melt crystallization section for carrying out at least one dynamic melt crystallization stage with the crude acrylic acid composition to prepare a first purified acrylic acid composition and a first residue, wherein the first melt crystallization section has an inlet for the crude acrylic acid composition, an outlet for the first purified acrylic acid composition and an outlet for the first residue, wherein the outlet for the first purified acrylic acid composition and the outlet for the first residue may be the same,
  means for adding a solvent to the first residue and for adjusting a predetermined weight ratio of the solvent to the first residue to prepare a ratio-adjusted residue and
  a second melt crystallization section for carrying out at least one further dynamic melt crystallization stage or at least one static melt crystallization stage with the first residue to prepare a second purified acrylic acid composition and a second residue, wherein the second melt crystallization section has an inlet being arranged downstream of the means for introducing the solvent to the first residue and the inlet being in fluid communication with the outlet for the first purified acrylic acid composition.

Preferably, the apparatus further comprises an outlet for the second purified acrylic acid composition and an outlet for the second residue.

Surprisingly it has been found that the apparatus of the present invention is simpler and less complex versus that disclosed in EP 1 150 759 B1, which requires a separator or filter [Abscheidevorrichtung (51) or Filter (51) in EP '759] in which the solids are retained so that the molten material may be refer to the crystallizer. Therefore preferred embodiments of the present invention will lack such a solid-liquid separator or filter in fluid communication with either the first or the second melt crystallization section.

It has to be noted that the outlet for the first purified acrylic acid composition and the outlet for the first residue may be the same, i.e. that the first melt crystallization section has one outlet for the first purified acrylic acid composition as well as for the first residue. Likewise, the outlet for the second purified acrylic acid composition and the outlet for the second residue may be the same. For falling film or static melt crystallization, the outlets in each case (first or second purified acrylic acid composition) will be the same, as these are batch operations. In contrast, the outlets will be different in the case of suspension crystallization, as the outlet for the first purified acrylic acid composition will be in communication with an inlet of the second melt crystallization section via an intermediate solid-liquid separation unit.

In a preferred embodiment, both the first and second melt crystallization sections lack additional outlets, in particular they lack outlets for gaseous solvent removal. Such lack of outlets for gaseous solvent and their accompanying overhead systems having condensers simplifies the construction and operation of the apparatus.

The first melt crystallization section comprises at least one dynamic melt crystallizer and preferably two to four dynamic melt crystallizers. As dynamic melt crystallizer(s), preferably, a falling film crystallizer, a fully flowed-through tube or a suspension crystallizer is used, wherein a falling film crystallizer is particularly preferred.

The apparatus may further comprise a first conduit for discharging the first residue from the first melt crystallization section, the first conduit being in fluid communication with the outlet for the first residue. The location of the means for adding the solvent to the first residue is not particularly limited. In order to achieve an efficient mixing of the solvent and the first residue, the means is preferably configured to introduce the solvent into the first conduit. With this respect, as non-limiting examples, the means for introducing the solvent into the first conduit may be provided in such a manner that the solvent is introduced into the conduit directly at the outlet for the first residue of the first melt crystallization section and/or downstream of this outlet.

In accordance with a further embodiment of the present invention, the apparatus further comprises a vessel, which is in fluid communication with the outlet for the first residue or with the first conduit for introducing first residue into the vessel, wherein the tank further comprises means for adding the solvent to the vessel. In addition, the vessel comprises an outlet, which is in fluid communication with the outlet for the first residue or with the first conduit for transferring the mixture of first residue and solvent from the vessel into the outlet for the first residue or the first conduit, respectively. This embodiment allows a particular good pre-mixing of the first residue and the solvent.

The second melt crystallization section may comprise one or more dynamic melt crystallization stage(s) or one or more static melt crystallization stage(s) for crystallizing the first residue to prepare a second purified acrylic acid composition and a second residue, wherein the second melt crystallization section has an inlet being arranged downstream of the means for introducing the solvent and being in fluid communication with the first conduit, an outlet for the second purified acrylic acid composition and an outlet for the second residue. In the case that the second melt crystallization section is configured for carrying out at least one dynamic melt crystallization stage, the second melt crystallization section may comprise at least one dynamic melt crystallizer, such as, for example, a falling film crystallizer, a fully flowed-through tube or a suspension crystallizer, of which a falling film crystallizer is preferred. In the case that the second melt crystallization section is configured for carrying out at least one static melt crystallization stage, the second melt crystallization section may comprise at least one static melt crystallizer, wherein the type of the static melt crystallizer is not particularly limited. It is particularly preferred that all crystallizers of the second melt crystallization section are static crystallizers.

In general, the apparatus may comprise a second conduit for recycling at least a part of the second purified acrylic acid composition to the first melt crystallization section, wherein the second conduit is in fluid communication with the outlet for the second purified acrylic acid composition of the second melt crystallization section and with an inlet for a second purified acrylic acid composition of the first melt crystallization section.

In a further preferred embodiment, the first melt crystallization section has two to four dynamic melt crystallizers and the second melt crystallization section has one to three static melt crystallizers. At least one of the dynamic melt crystallizers and preferably all of the dynamic melt crystallizers are a falling film crystallizer, a fully flowed-through tube or a suspension crystallizer, wherein a falling film crystallizer is particularly preferred.

In an alternative embodiment, the apparatus is configured so that the first melt crystallization section comprises only one dynamic melt crystallizer and that the second melt crystallization section comprises only one static melt crystallizer. Again, the dynamic melt crystallizer may be a falling film crystallizer, a fully flowed-through tube or a suspension crystallizer, wherein a falling film crystallizer is particularly preferred.

In general and independently from the specific configuration of the first and the second melt crystallization sections, the means for introducing the solvent into the first conduit preferably comprises a piping for supplying the solvent, a control valve and a flow meter.

Preferably the apparatus does not comprise any additional separation means for separating precipitated maleic anhydride from the crude acrylic acid composition or from the first residue, such as, for example, a filter. Such additional separation means is in general not required in context with the process of the present invention, which allows to keep the maleic anhydride in solution and prevents a precipitation thereof.

Specific embodiments in accordance with the present invention are subsequently described with reference to the appended drawings, in which:

FIG. 1 schematically shows an apparatus for conducting the process for the purification of the crude acrylic acid composition in accordance with an embodiment of the present invention.

Figure 2:
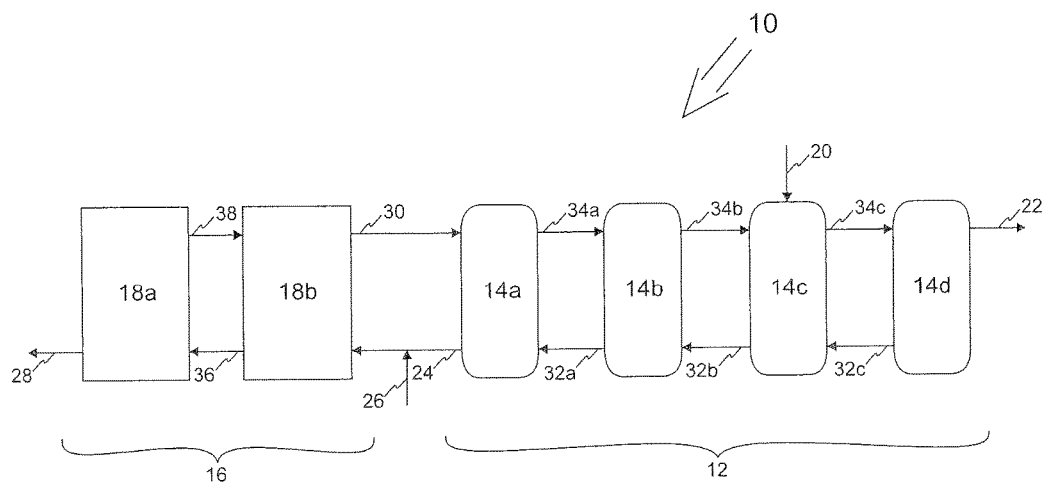

FIG. 2 schematically shows an apparatus for conducting the process for the purification of the crude acrylic acid composition in accordance with another embodiment of the present invention.

FIG. 1 shows an apparatus 10 for conducting the process for the purification of the crude acrylic acid composition in accordance with an embodiment of the present invention. The apparatus includes a first melt crystallization section 12 which comprises only one falling film crystallizer 14 as a dynamic melt crystallizer. In addition, the apparatus 10 comprises a second melt crystallization section 16 having only one static melt crystallizer 18. The falling film crystallizer 14 is connected with a feed conduit 20 which is suitable for feeding a crude acrylic acid composition into the falling film crystallizer 14. In addition, the falling film crystallizer 14 has a discharge conduit 22 for the discharge of a first purified acrylic acid composition from the falling film crystallizer 14 and from the apparatus 10. The static melt crystallizer 18 is connected with the falling film crystallizer 14 via a transfer conduit 24 which is suitable for transferring a first residue obtained by crystallization in the falling film crystallizer 14 into the static melt crystallizer 18. With this respect, the transfer conduit 24 is in fluid communication with both the falling film crystallizer 14 and the static melt crystallizer 18. A solvent conduit 26, which is configured for feeding a solvent, discharges into the transfer conduit 24 such that a solvent can be added to the first residue while it is transferred from the falling film crystallizer 14 to the static melt crystallizer 18. The static melt crystallizer 18 comprises a discharge conduit 28 which serves for discharging a second residue, which is obtained by the crystallization in the static melt crystallizer 18 from the static melt crystallizer 18 and from the apparatus 10. A recycle conduit 30 provides a fluid communication between the static melt crystallizer 18 and the falling film crystallizer 14 and therefore allows to recycle at least a part of the second purified acrylic acid composition, which results from the crystallization in the static melt crystallizer 18, back into the falling film crystallizer 14.

During operation of the apparatus 10 shown in FIG. 1, a crude acrylic acid composition is introduced into the falling film crystallizer 14 through the feed conduit 20. A falling film crystallization is performed in the falling film crystallizer 14, which leads to a first purified acrylic acid composition and a first residue. The first purified acrylic acid composition is removed from the falling film crystallizer 14 and from the apparatus 10 via the discharge conduit 22, whereas the first residue is discharged from the falling film crystallizer 14 via the transfer conduit 24. In the transfer conduit 24 a solvent, preferably water, is added to the first residue via the solvent conduit 26 so that the weight ratio of the solvent to the maleic anhydride is adjusted to 0.3 or more in order to prepare a ratio-adjusted residue. The ratio-adjusted residue is fed via the transfer conduit 24 into the static melt crystallizer 18, where it is subjected to static melt crystallization, which leads to the preparation of a second purified acrylic acid composition and a second residue. While the second residue is discharged from the static melt crystallizer 18 and from the apparatus 10 via the discharge conduit 28, the second purified acrylic acid composition obtained in the static crystallization leaves the static melt crystallizer 18 through the recycle conduit 30 and is recycled back into the falling film crystallizer 14.

In FIG. 2 an apparatus 10 is shown, wherein the first melt crystallization section 12 comprises four falling film crystallization stages 14a, 14b, 14c and 14d and wherein the second melt crystallization section 16 includes two static melt crystallization stages 18a and 18b. There are provided transfer conduits 32a, 32b and 32c between the falling film crystallization stages 14a, 14b, 14c and 14d, through which a residue obtained by falling film crystallization can be transferred from one of the falling film crystallization stages to the respective downstream falling film crystallization stage. In addition, the falling film crystallization stages 14a, 14b, 14c and 14d are connected via recycle conduits 34a, 34b and 34c suitable for recycling at least a part of the purified acrylic acid composition from one of the falling film crystallization stages to the respective upstream falling film crystallization stage. A feed conduit 20 is connected to the falling film crystallization stage 14c such that a crude acrylic acid composition can be introduced into the falling film crystallization stage 14c. A discharge conduit 22 is provided at the falling film crystallization stage 14d in order to remove a first purified acrylic acid composition from the apparatus 10. A transfer conduit 24 provides a fluid communication between the falling film crystallization stage 14a of the first melt crystallization section 12 and the static melt crystallization stage 18b of the second melt crystallization section 16 so that a first residue obtained by the crystallization in the falling film crystallization stages 14a, 14b, 14c and 14d can be transferred into the static melt crystallization stage 18b. A solvent conduit 26, which is suitable for feeding a solvent, discharges into the transfer conduit 24 such that a solvent can be added to the first residue while it is transferred from the falling film crystallization stage 14a to the static melt crystallization stage 18b. The static melt crystallization stages 18a and 18b are connected via a transfer conduit 36 for transferring a residue obtained by crystallization from the static melt crystallization stage 18b to the static melt crystallization stage 18a. In addition, the static melt crystallization stage 18a and the static melt crystallization stage 18b are connected via a recycle conduit 38 allowing for transferring a purified acrylic acid composition, which results from the crystallization in the static melt crystallization stage 18a, into the static melt crystallization stage 18b. Furthermore, the static melt crystallization stage 18a comprises a discharge conduit 28 for discharging a second residue, which is obtained by crystallization in the static melt crystallization stages 18a and 18b, from the apparatus 10. A recycle conduit 30 provides a fluid communication between the static melt crystallization stage 18b and the falling film crystallization stage 14a, which is suitable for transferring a second purified acrylic acid composition resulting from the crystallization in the static melt crystallization stages 18a and 18b of the second melt crystallization section 16, back into the falling film crystallization stage 14a of the first melt crystallization section 12.

During operation of the apparatus 10 shown in FIG. 2 a crude acrylic acid composition is fed into the falling film crystallization stage 14c via the feed conduit 20. In each of the falling film crystallization stages 14a, 14b, 14c and 14d a purified acrylic acid composition and a residue are prepared. Each of the residues obtained in one of the falling film crystallization stages 14b, 14c and 14d is transferred via the transfer conduits 32a, 32b and 32c to the respective downstream falling film crystallization stage. In addition, each of the purified acrylic acid compositions obtained in one of the falling film crystallization stages 14a, 14b and 14c is at least partially recycled via the recycle conduits 34a, 34b and 34c to the respective upstream falling film crystallization stage. The residue obtained after the crystallization in the falling film crystallization stage 14a of the first melt crystallization section 12 is the first residue and is transferred via the transfer conduit 24 into the static melt crystallization stage 18b of the second melt crystallization section 16. During the transfer a solvent, preferably water, is added to the first residue via the solvent conduit 26 so that the weight ratio of the solvent to the maleic anhydride is adjusted to 0.3 or more to prepare a ratio-adjusted residue. The ratio-adjusted residue undergoes static melt crystallization in the static melt crystallization stages 18a and 18b, wherein in each of the static melt crystallization stages 18a and 18b a purified acrylic acid composition and a residue are prepared. The residue obtained in the static melt crystallization stage 18b is transferred via the transfer conduit 36 to the downstream static melt crystallization stage 18a. In addition, the purified acrylic acid composition obtained in the static melt crystallization stage 18a is at least partially recycled via the recycle conduit 38 into the upstream static melt crystallization stage 18b. The purified acrylic acid composition obtained after the crystallization in the static melt crystallization stage 18b, which is the second purified acrylic acid composition, is recycled via the recycle conduit 30 into the falling film crystallization stage 14a of the first melt crystallization section 12. A finally purified acrylic acid composition, which is the first purified acrylic acid composition, is removed from the falling film crystallizer 14d and from the apparatus 10 via the discharge conduit 22, while a final residue, which is the second residue, is removed from the static melt crystallization stage 18a and from the apparatus 10 via the discharge conduit 28.

Subsequently, the present invention is described by means of an illustrative but non-limiting example and a comparative example.

Example

The following example is provided to illustrate the invention and does not limit the scope of the claims. Unless stated otherwise, all parts and percentages are by weight.

A crude acrylic acid composition containing maleic anhydride as an impurity was produced by a propylene route and subsequently purified by means of dynamic melt crystallization to prepare a first purified acrylic acid composition and a first residue. The first residue obtained in this way contained 3.92% of maleic anhydride and 0.69% of water, leading to a weight ratio of water to maleic anhydride of 0.18, which is less than 0.3.

Water as a solvent was added to the first residue in an amount that the weight ratio of the solvent to the maleic anhydride was 0.80. Due to this, at least part of the maleic anhydride was hydrolyzed to maleic acid, whereas the rest was reliably kept in solution. The resulting ratio-adjusted residue was further purified by means of static melt crystallization to prepare a second purified acrylic acid composition and a second residue.

The compositions of the feed, of the $1^{st}$ purified acrylic acid composition, of the $1^{st}$ residue, of the ratio-adjusted residue, of the $2^{nd}$ purified acrylic acid composition and of the $2^{nd}$ residue are summarized in the subsequent table.

|  | Feed | $1^{st}$ purified acrylic acid composition | $1^{st}$ residue | Ratio-adjusted residue | $2^{nd}$ purified acrylic acid composition | $2^{nd}$ residue |
|---|---|---|---|---|---|---|
| Acrylic acid | 99.46 | 99.94 | 87.50 | 85.43 | 94.50 | 50.50 |
| Dimer | 0.02 | 0.00 | 0.45 | 0.44 | 0.19 | 1.39 |
| Maleic anhydride/ Maleic acid | 0.16 | 0.00 | 3.92 | 3.82 | 1.71 | 12.06 |
| Water | 0.03 | 0.02 | 0.69 | 3.05 | 0.62 | 12.51 |
| Furfural | 0.03 | 0.00 | 0.76 | 0.74 | 0.33 | 2.35 |
| Benzaldehyde | 0.02 | 0.00 | 0.55 | 0.53 | 0.24 | 1.69 |
| Propionic acid | 0.04 | 0.01 | 0.88 | 0.86 | 0.39 | 2.69 |
| Acetic acid | 0.08 | 0.01 | 1.60 | 1.57 | 0.71 | 4.92 |
| Acrolein | 0.12 | 0.00 | 2.94 | 2.87 | 1.28 | 9.04 |
| Others | 0.04 | 0.02 | 0.71 | 0.69 | 0.03 | 2.85 |
| Water to maleic anhydride |  |  | 0.18 | 0.80 |  |  |

Comparative Example

The same method as described above for the example was repeated except that no water as a solvent was added to the first residue.

The further purification of the first residue by means of static melt crystallization resulted in an accumulation of maleic anhydride in the crystallization equipment thereby blocking the conduits and valves of the same.

REFERENCE NUMERAL LIST

10 Apparatus
12 First melt crystallization section
14, 14a, 14b, 14c, 14d Falling film crystallizer/falling film crystallization stages
16 Second melt crystallization section
18, 18a, 18b Static melt crystallizer/static melt crystallization stages
20 Feed conduit
22 Discharge conduit
24 Transfer conduit between falling film crystallizer/falling film crystallization stage and static melt crystallizer/static melt crystallization stage
26 Solvent conduit
28 Discharge conduit
30 Recycle conduit between static melt crystallizer/static melt crystallization stage and falling film crystallizer/falling film crystallization stage
32a, 32b, 32c Transfer conduit between falling film crystallizers/falling film crystallization stages
34a, 34b, 34c Recycle conduit between falling film crystallizers/falling film crystallization stages
36 Transfer conduit between static melt crystallizers/static melt crystallization stages
38 Recycle conduit between static melt crystallizers/static melt crystallization stages

The invention claimed is:

1. An apparatus (10) for the purification of a crude acrylic acid composition containing maleic anhydride as an impurity being configured for carrying out a melt crystallization process comprising the steps of:
    (a) carrying out at least one dynamic melt crystallization stage (14, 14a, 14b, 14c, 14d) with the crude acrylic acid composition to prepare a first purified acrylic acid composition and a first residue containing at least 3.5% by weight maleic anhydride,
    (b) adding a solvent (26) which is capable of dissolving maleic anhydride to the first residue in an amount that the weight ratio of the solvent to the maleic anhydride is 0.3 or more to prepare a ratio-adjusted residue, and
    (c) carrying out at least one further dynamic melt crystallization stage and/or at least one static melt crystallization stage (18, 18a, 18b) with the ratio-adjusted residue to prepare a second purified acrylic acid composition and a second residue,
    wherein the apparatus (10) comprises:
        a first melt crystallization section (12) for (a) carrying out at least one dynamic melt crystallization stage (14, 14a, 14b, 14c, 14d) with the crude acrylic acid composition to prepare a first purified acrylic acid composition and a first residue, wherein the first melt crystallization section (12) has an inlet for the crude acrylic acid composition, an outlet for the first purified acrylic acid composition and an outlet for the first residue, wherein the outlet for the first purified acrylic acid composition and the outlet for the first residue may be the same,
        means (26) for (b) adding a solvent to the first residue and for adjusting a predetermined weight ratio of the solvent to the first residue to prepare a ratio-adjusted residue and
        a second melt crystallization section (16) for (c) carrying out at least one further dynamic melt crystallization stage or at least one static melt crystallization stage (18, 18a, 18b) with the first residue to prepare a second purified acrylic acid composition and a second residue, wherein the second melt crystallization section (16) has an inlet being arranged downstream of the means (26) for introducing the solvent to the first residue and the inlet being in fluid communication with the outlet for the first purified acrylic acid composition.

2. The apparatus (10) of claim 1, wherein the at least one dynamic melt crystallizer (14) is a falling film crystallizer.

3. The apparatus (10) of claim 1, wherein the means (26) for introducing the solvent comprise a piping for supplying the solvent, a control valve and a flow meter.

4. The apparatus (10) of claim 1, wherein the apparatus (10) does not comprise any separation means for separating a precipitated maleic anhydride from the crude acrylic acid composition or from the first residue.

5. A process for the purification of a crude acrylic acid composition containing maleic anhydride as an impurity, the process comprising the steps of:
    (a) carrying out at least one dynamic melt crystallization stage (14, 14a, 14b, 14c, 14d) with the crude acrylic acid composition to prepare a first purified acrylic acid composition and a first residue containing at least 3.5% by weight maleic anhydride,
    (b) adding a solvent (26) which is capable of dissolving maleic anhydride to the first residue in an amount that the weight ratio of the solvent to the maleic anhydride is 0.3 or more to prepare a ratio-adjusted residue and
    (c) carrying out at least one further dynamic melt crystallization stage and/or at least one static melt crystallization stage (18, 18a, 18b) with the ratio-adjusted residue to prepare a second purified acrylic acid composition and a second residue,
wherein at least one of steps (a), (b), or (c) is performed in the apparatus of claim 1.

6. The process of claim 5, wherein the concentration of maleic anhydride in the first residue prepared in step (a) is at least 4% by weight based on 100% by weight of the first residue.

7. The process of claim 5, wherein the weight ratio of the solvent to the maleic anhydride in step (b) is adjusted to a range of from 0.3 to 2.0.

8. The process of claim 5, wherein the solvent is water.

9. The process of claim 5, wherein the second purified acrylic acid composition obtained in step (c) (18, 18a, 18b) is at least partially recycled (30) to the dynamic melt crystallization of step (a) (14, 14a, 14b, 14c, 14d).

10. The process of claim 5, wherein two to four dynamic melt crystallization stages (14a, 14b, 14c, 14d) are used to prepare the first purified acrylic acid composition and the first residue in step (a) and wherein one to three static melt crystallization stages (18a, 18b) are carried out with the ratio-adjusted residue in step (c).

11. The process of claim 10, wherein at least one of the dynamic melt crystallization stages (14a, 14b, 14c, 14d) of step (a) is carried out as falling film crystallization.

12. The process of claim 5, wherein the crude acrylic acid composition is produced from propylene.

13. The process of claim 5, wherein the crude acrylic acid composition is obtained by a synthesis process comprising at least one fermentation step.

14. The process of claim 5, wherein no additional solvent is added to the crude acrylic acid composition before it is subjected to step (a).

15. The process of claim 5, wherein in steps (a) to (c) no separation of a precipitated maleic anhydride by a separation means from the crude acrylic acid composition or from the first residue is conducted.

* * * * *